(12) United States Patent
Aberg et al.

(10) Patent No.: US 8,741,930 B2
(45) Date of Patent: Jun. 3, 2014

(54) TREATING XEROPHTHALMIA WITH NORKETOTIFEN

(75) Inventors: A. K. Gunnar Aberg, Sarasota, FL (US); Keith Johnson, Durham, NC (US)

(73) Assignee: Bridge Pharma, Inc., Sarasota, FL (US)

( * ) Notice: Subject to any disclaimer, the term of this patent is extended or adjusted under 35 U.S.C. 154(b) by 0 days.

(21) Appl. No.: 12/317,575

(22) Filed: Dec. 24, 2008

(65) Prior Publication Data

US 2010/0105734 A1    Apr. 29, 2010

Related U.S. Application Data

(60) Provisional application No. 61/197,177, filed on Oct. 24, 2008.

(51) Int. Cl.
*A61K 31/4535* (2006.01)

(52) U.S. Cl.
USPC .......................................... 514/324; 514/912

(58) Field of Classification Search
USPC ................................. 514/324, 912
See application file for complete search history.

(56) References Cited

U.S. PATENT DOCUMENTS

| | | | |
|---|---|---|---|
| 4,844,902 A | 7/1989 | Grohe | |
| 5,369,095 A | 11/1994 | Kee et al. | |
| 5,624,893 A | 4/1997 | Yanni | |
| 5,776,445 A | 7/1998 | Cohen et al. | |
| 5,939,426 A | 8/1999 | McCullough | 514/290 |
| 6,207,684 B1 | 3/2001 | Aberg | 514/324 |
| 6,455,547 B1 | 9/2002 | Kis | |
| 6,776,982 B2 | 8/2004 | Kis et al. | |
| 7,226,934 B1 | 6/2007 | Aberg et al. | 514/324 |
| 7,247,623 B2 | 7/2007 | Yerxa et al. | 514/214.02 |
| 7,270,830 B2 | 9/2007 | Reidenberg et al. | 424/449 |
| 7,557,128 B2 | 7/2009 | Aberg et al. | |
| 2002/0037883 A1* | 3/2002 | Singh | 514/171 |
| 2006/0148899 A1* | 7/2006 | Green et al. | 514/554 |
| 2007/0014797 A1 | 1/2007 | Hitraya | 424/144.1 |
| 2007/0112026 A1 | 5/2007 | Nagamoto et al. | 514/312 |
| 2008/0085263 A1 | 4/2008 | Thuresson et al. | 424/85.7 |
| 2008/0139531 A1 | 6/2008 | Yanni et al. | |
| 2009/0269369 A1* | 10/2009 | Doi et al. | 424/195.18 |
| 2009/0286718 A1* | 11/2009 | Stringer | 514/11 |
| 2010/0105734 A1 | 4/2010 | Aberg et al. | |
| 2010/0130550 A1 | 5/2010 | Aberg et al. | |

FOREIGN PATENT DOCUMENTS

WO    2005/000307 A1    1/2005

OTHER PUBLICATIONS

Final Rejection mailed Oct. 31, 2011 in co-pending U.S. Appl. No. 12/622,509.
International Search Report/Written Opinion dated Jan. 13, 2010 in co-pending foreign patent application PCT/US2009/65252.
Notification and International Preliminary Report on Patentability/Written Opinion dated Jun. 3, 2011 in co-pending foreign patent application PCT/US2009/065252.
Acta Ophthalmologica 2008: 86: 716-726, "Detrimental effect of preservatives in eyedrops: implications for the treatment of glaucoma", Baudouin.
Investigative Ophthalmology & Visual Science, Dec. 1983, vol. 24, pp. 1624-1626, "Human Tears: Osmotic Characteristics", Benjamin, et al.
Handbook of Ocular Disease Management, 2009, http://www.revoptom.com/handbook/sect3h.htm, 1 page, "Chemical Burns", Dr. Wright Productions.
Chem. Pharm. Bull. 54(11), 1500-1507 (2006), "Optimization and Physicochemical Characterization of Thermosensitive Poloxamer Gel Containing Puerarin for Ophthalmic Use", Qi, et al.
J. Soc. Cosmet. Chem. 1962, 13: 281-289, "Interpretation of Eye Irritation Tests", Kay, et al.
Research and Clinical Forums 4: 17-20, 1982, "Metabolism and pharmacokinetics of ketotifen in children", Kennedy.
US Pharmacopeia Convention, 2000: 1809; 3 pages, "Chpt. 51, Antimicrobial Effectiveness Testing", http://www.pharmacopeia.cn/v29240/usp29nf24s0_c51.html.
US Pharmacopeia Excipient Verification Program, Manual, US Pharmacopeial Convention, V.2.0. Oct. 2009, NF21, -p. 21, 33, 74.
US Pharmacopeia Excipient Drug Substance Verification Program, Manual, US Pharmacopeial Convention, V.3.1., Dec. 2007, p. 1, 29.
Wikipedia, "Conjunctivitis", http://en.wikipedia.org/wiki/Conjunctivitis, 4 pages, Oct. 24, 2009.
Wikipedia, "Keratitis", http://en.wikipedia.org/wiki/Keratitis, 3 pages, Sep. 18, 2009.
Office Action dated Apr. 15, 2011 in co-pending U.S. Appl. No. 12/622,509
Office Action dated Dec. 20, 2011 in co-pending U.S. Appl. No. 12/622,509.
International Preliminary Examination Report dated Oct. 28, 2010 in corresponding application (PCT/US2008/014056).
Alcon: Dry Eye Information, 2008. www.systane.com/eyecare-professional/Tear-Film-Break-Up-Time.asp.
Br J Ophthalmol 2002; 86: 181-184; Pasquale Aragona et al.; "Long term treatment with sodium hyaluronate-containing artificial tears reduces ocular surface damage in patients with dry eye".
Association for Research for Research in Vision & Ophthalmology (ARVO), 2008; Abstract #6316; JL Boyer et al. "Assessment of Antimuscarinic Activity of Topical and Oral Antihistamines".
Therapeutic Review; Review of Optometry; Special Edition. Sep. 2007: 48-52.; Ernest L. Bowling; "Contact Lens-Related Dry Eye".
Dry eye disease: The scale of the problem; CAT.INIST; Survey of Ophthalmology, 2001, 45: S199-S202 (Abstract); Brewitt Horst et al.
CibaVision. ZADITOR. Information to patients.
Effect of age on tear osmolality; CAT.INIST; Optometry and vision science. 1995, 72: 713-717 (Abstract); Craig J.P. et al.

(Continued)

*Primary Examiner* — Zohreh Fay
(74) *Attorney, Agent, or Firm* — Cantor Colburn LLP

(57) ABSTRACT

Methods of using a cycloheptathiophene compound for the treatment of xerophthalmia are described, as are formulations and compositions for such treatment.

18 Claims, No Drawings

(56) References Cited

OTHER PUBLICATIONS

J.Pharmacol. Exp Therap. 1944, 82: 377-390; John H. Draize et al.; "Methods for the Study of Irritation and Toxicity of Substances Applied Topically to the Skin and Mucous Membranes".

Improvement of the ocular surface using hypotonic 0.4% hyaluronic acid drops in keratoconjunctivitis sicca; CAT.INIST; Eye 2000, 14: 892-898 (Abstract); Lester, Michele et al.

Am J. Manag Care. Apr. 2008; 14 (2 Suppl): S88-101; Lemp MA: "Management of dry eye disease"; (Abstract).

Curr Med Res Opin 20(8): 1167-1173, 2004; Andrea Leonardi et al.; "Efficacy and Comfort of Olopatadine Versus Ketotifen Ophthalmic Solutions: A Double-Masked, Environmental Study of Patient Preference".

Arch Ophthalmol. 2000; 118: 1264-1268; Scot E. Moss et al.; "Prevalence of and Risk Factors for Dry Eye Syndrome".

The Merck Manual, 18$^{th}$ Edition, pp. 899-900; 102 Corneal Disorders; *Keratoconjunctivitis sicca*.

http://www.ophmanagement.com/article.aspx?article=86656; Ophthalmology Management, Sep. 2006; Robert J. Noecker et al.; "Understand the Impact of BAK on Glaucoma Patients".

Agents Actions. Apr. 1988; 23(3-4): 173-176; Nolte H. et al. "Inhibition of basophil histamine release by methotrexate".

Clin Ther. 2007, 29: 611-616 (Abstract); Ousler GW 3$^{rd}$ etl al.; "An open-label, investigator-masked, crossover study of the ocular drying effects of two antihistamines, topical epinastine and systemic loratadine, in adult volunteers with seasonal allergic conjunctivitis".

Patanol, Alcon Laboratories, Inc.; Packet Insert, 2007.

Current Medical Research and Opinion, vol. 21, No. 9, Sep. 2005, pp. 1377-1388 (12) (Abstract); Rosenwasser, Lanny J. et al. "Mast cell stabilization and anti-histamine effects of olopatadine ophthalmic solution: a review of pre-clinical and clinical research".

Eye Facts; University of Illinois. Allergic Conjunctivitis www.uic.edt/com/eye/LearningAboutVision/EyeFacts/Allergic-Conjunctivitis.shtml.

Helvetica Chimica Acta—vol. 59, (1976);pp. 866-877; Waldvogel E. et al.; "Untersuchungen uber syntehtische Arzueimittel 9- und 10-Oxo-Derivate von 9, 10-Dihydro-4H-benzo[4,5]cyclohepta-{1,2-b] thiophene".

Wikipedia *Keratoconjunctivitis sicca*; Oct. 2008; http://en.wikipedia.org/wiki/Keratoconjunctivitis_sicca.

Evaluation of muscarinic receptor antagonism by antihistamines, Abstract, XXVI EAACI Congress, 2007. Wolff SC et al.

International Search Report dated Mar. 4, 2009.

The CLAO Journal; Oct. 1995; vol. 21, No. 4; pp. 221-232; Michael A. Lemp; "Report of the National Eye Institute/Industry Workshop on Clinical Trials in Dry Eyes".

Progress in Retinal and Eye Research, vol. 29, 2010, pp. 312-334, "Preservatives in eyedrops: The good, the bad, and the ugly", Baudouin, et al.

Graefe's Arch Clin Exp Ophthalmol, vol. 241, 2003, pp. 1037-1043, "In vitro effects of preserved and unpreserved antiglaucoma drugs on apoptotic marker expression by human trabecular cells", Hamard, et al.

European Medicines Agency, EMEA Public Statement on Antimicrobial Preservatives in Ophthalmic Preparations for Human Use, Dec. 8, 2009, 1 page.

Acta Ophthalmol. 2008: 86: 716-726, "Detrimental effect of preservatives in eyedrops: implications for the treatment of glaucoma", Baudouin.

Rapid Communications in Mass Spectrometry, 2003, vol. 17, pp. 2459-2463, "Determination of ketotifen and its conjugated metabolite in human plasma by liquid chromatography/tandem mass spectrometry: application to a pharmacokinetic study", Chen, et al.

Emadine; Drugs.com; Feb. 2006—3-pages.

Curr Med Res Opin. 2003; 19(4): 313-320; I.G. V. James et al.; "Comparison of the Efficacy and Tolerability of Topically Administered Azelastine, Sodium Cromoglycate and Placebo in the Treatment of Seasonal Allergic Conjunctivitis and Rhino-Conjunctivitis".

Life Sciences, vol. 40, No. 9, 1987, pp. 883-890; Pergamon Journals; J.F. Le Bigot et al.; "Species Differences in Metabolism of Ketotifen in Rat, Rabbit and Man: Demonstration of Similar Pathways In Vivo and in Cultered Hepatocytes".

DailyMed: About DailyMed; Patanol; Nov. 2007—2-Pages.

Arbrecht v. Graefes Arch. klin. exp. Ophthal. 192, 141-150; (Jul. 2,1974); Wolfgang Scherz et al.; "Tear Volume in Normal Eyes and *Keratoconjunctivitis sicca*\*" 1-Page.

Eye & Contact Lens: Science & Clinical Practice: Dec. 2006—vol. 32—Issue 6—pp. 272-276; Arturo L. Villareal et al.; "Effect of Topical Ophthalmic Epinastine and Olopatadine on Tear Volume in Mice" 1-Page.

Novartis Zaditor packet insert; Oct. 2002—4-Pages.

CIBA Vision, A Novartis Company, "Zaditor: ketotifen fumarate ophthalmic solution, 0.025%", packet insert, 2002, 3 pages, Information to Patients.

Merck Research Laboratories, The Merck Manual of Diagnosis and Therapy, 2006, Eighteenth Edition, 102 Corneal Disorders, "*Keratoconjunctivitis sicca*", pp. 899-900, Beers, et al.

Eye Facts, University of Illinois, "Allergic Conjunctivitis", 3 pages, Jul. 1, 1990, http://www.uic.edu/com/eye/LearningAboutVision/EyeFacts/AllergicConjunctivitis.shtml.

"*Keratoconjunctivitis sicca*"; The Merck Manual_18th Edition; by Merck & Co., Inc.; Corneal Disorders; p. 899-900; (2006).

Patanol (olopatadine hydrochloride ophthalmic solution 0.1%; from Alcon Laboratories; 1 page package insert; Jan. 2007.

International Search Report, Written Opinion and IPRP; International Application PCT/US2009/65252; International Fling Date Nov. 20, 2009; Date of Mailing Jan. 13, 2010; 11 pages.

Gardner, Susanne; "What About the BAK?"; Advanced Ocular Care; May/Jun. 2011, pp. 31-33; (2011).

\* cited by examiner

TREATING XEROPHTHALMIA WITH NORKETOTIFEN

This application claims priority of provisional application Ser. No. 61/197,177, filed Oct. 24, 2008, the disclosure of which is hereby incorporated by reference.

FIELD

Xerophthalmia is an eye disease in mammals and in particular in humans, which causes may include decreased tear production, increased tear film evaporation and/or contact lens intolerance. This disease is alternatively called "dry eye disease" or "dry eye syndrome" or "dry eyes" or "keratoconjunctivitis sicca" or "xerophthalmic disorder" and although the terms may represent various forms of this disorder, the terms are used interchangeably herein and are considered as synonyms in this document. All forms of dry eye disease result in dehydration of the mucous membranes of the eye and of the adjacent mucosal surfaces (Lemp M A, 1995; which publication is hereby incorporated in its entirety by reference). The symptoms of xerophthalmia may vary between patients, but include one or more symptoms, such as for example ocular dryness, ocular burning, sandy-gritty eye irritation, ocular foreign-body sensation and photophobia (Keratoconjunctivitis sicca. Wikipedia, October 2008; which publication is hereby incorporated in its entirety by reference.)

Chemically, norketotifen is a cycloheptathiophene compound, called (RS)-4-(4-piperidyliden)-9-oxo-9,10-dihydro-4H-benzo[4,5]cyclohepta[1,2-b]thiophene and is a racemic mixture of two isomers. The chemical structure is shown herein.

The use of norketotifen in patients suffering from allergic conjunctivitis and similar ocular disorders is described in U.S. Pat. No. 6,207,684, and the single isomers were described in U.S. Pat. No. 7,226,934, the disclosures of which are hereby incorporated by reference.

It has now surprisingly been found that norketotifen is therapeutically valuable for the treatment of dry eye disease and the embodiments disclosed herein relate to methods of reducing ocular dryness, relieving dry eye symptoms, increasing tear flow, and/or decreasing contact lens intolerance. Embodiments include the administration of norketotifen to mammals suffering from dry eyes.

BACKGROUND

The overall prevalence of dry eyes was found to be 14.4% in a cohort aged 48 to 91 years (Moss et al., 2000, which publication is hereby incorporated in its entirety by reference). It has also been estimated that one in four patients consulting ophthalmologists complain of dry eyes and up to 20% of adults aged 45 years and older experience dry eye symptoms (Brewitt et al., 2001; which publication is hereby incorporated in its entirety by reference).

Contact lenses provide a valuable option to the vision impaired. Although contact lenses have been much improved, irritation is still a common problem and wearers often experience symptoms of xerophthalmia due to moisture loss from the contact lenses (Bowling, 2007, which publication is hereby incorporated in its entirety by reference.)

Dry eye disease and the symptoms thereof are vastly different from allergic conjunctivitis and similar allergic, inflammatory or allergic/inflammatory diseases. The symptoms for dry eye disease include dryness, burning, sandy-gritty eye irritation, foreign-body sensation, photophobia (Keratoconjunctivitis sicca. Wikipedia, October 2008; which publication is hereby incorporated in its entirety by reference.) The most common symptoms for allergic conjunctivitis are red eyes and itching, which is associated with allergies and are related to release of histamine and other mediators (Allergic conjunctivitis. Eye facts. Univ. of Illinois; which publication is hereby incorporated in its entirety by reference.)

Ketotifen molecules can be demethylated in the liver, but not in the eye, to form norketotifen, which is therefore a hepatic metabolite of ketotifen. In the USA, ketotifen has received regulatory approval for the treatment of ocular allergies, and is marketed under the name Zaditen®, Novartis.

Pharmacological effects of norketotifen and are shown in Examples 1, 2, 3 and 4 of this document.

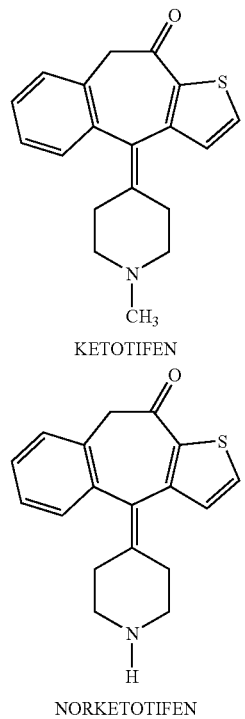

KETOTIFEN

NORKETOTIFEN

Ketotifen is available commercially from Sigma-Aldrich (Internet: Sigma-Aldrich.com/order). Norketotifen is not available commercially and was custom-made according to the method of Waidvogel et al. 1976, which publication is hereby incorporated in its entirety by reference.

Current Treatment of Dry Eye Disease

Current treatments of dry eye disease are reviewed by Lemp, 2008, which publication is hereby incorporated in its entirety by reference. It is pointed out by Lemp that artificial tears offer only a temporary palliative effect, while corticosteroids are effective disease-modifying agents for patients suffering from dry eye disorders. However, topical corticosteroids are not recommended for long-term use because of the known risks for significant adverse effects, which include increased intraocular pressure and the development of cataracts. Steroids useful for the treatment of xerophthalmia are for example rimexolone (Vexol®, Alcon), fluorometholone (generic), prednisolone acetate (generic), loteprednol etabonate (generic) and difluprednate (Durezol™, Sirion).

The only non-steroid drug that is presently approved in the US for the treatment of dry eyes is cyclosporine (Restasis®, Allergan), which is a potent immunosuppressive drug. The therapeutic effect of Restasis® have slow onset and full activity is obtained after twice daily use of the drug for up to 6 months. The manufacturer cites four clinical studies performed in approximately 1200 patients with moderate to severe dry eyes. 15 percent of Restasis®-treated patients experienced an improvement in Schirmer scores of 10 mm or greater compared to 5 percent of vehicle-treated patients. The most common side effect following the use of Restasis® is ocular burning, which according to the manufacturer occurred in 17 percent of Restasis®-treated patients (Physicians' Desk Reference, 2007, p. 575). Since cyclosporine is a potent immunosuppressive drug, and in light of the limited therapeutic success, ophthalmologists may not want to use this drug when ocular infections are present, which are not uncommon in patients suffering from dry eyes.

Drug-Induced Xerophthalmia

As a consequence of their pharmacological activity, drugs with anticholinergic effects, such as for example meclizine, desloratadine, diphenhydramine, oxybutynin and tolterodine can cause dry eyes. Also drugs that are being used for allergic conjunctivitis, may have potent antimuscarinic M-1 activity as described by Boyer et al., 2008, which publication is hereby incorporated in its entirety by reference.

Also the ocular drug olopatadine that is commonly used for allergic conjunctivitis and that is devoid of potent antimuscarinic activity, has been shown to reduce tear flow, as described in U.S. Pat. No. 7,247,623, which patent is incorporated herein its entirety by reference.

The antihistaminic drug ketotifen (Zaditen®, Novartis) has antimuscarinic (M-1) side effects as is shown in Example 3, below. The antihistaminic drug loratadine (Clarinex®, Schering) has also potent antimuscarinic activity (U.S. Pat. No. 5,939,426), whereby it may significantly decrease tear production (Ousler et al., 2007), both documents are hereby incorporated in their entirety by reference.

Antihistaminic Drugs and Tear Production

No human lacrimal histamine H-1 receptors have been found (Beuerman et al. 2004) and the effects of histamine H-1 antagonists on lacrimal tear production are therefore minimal or non-existent. The current finding that the compound norketotifen, which has antihistaminic activity, has the ability to significantly increase tear flow is surprising, particularly since such effects were not observed with the antihistaminic compound ketotifen.

SUMMARY

Pharmacological, physicochemical and pharmaceutical properties of norketotifen that may be related to the effects of this compound on xerophthalmia have now been studied. While ketotifen was found not to increase tear flow after topical administration to the eye, norketotifen was surprisingly found to increase tear flow (Example 4, below) after topical administration to the eyes of laboratory animals. Topical ocular formulations of norketotifen preferably contain norketotifen in concentrations between 0.01 percent and 0.50 percent, more preferably between 0.01 percent and 0.1 percent. Said formulations have acidity preferably between pH 4 and 7, more preferably between pH 4.6 to pH 6.0 and most preferred approximately pH 5.5. The preferred osmolality is between 150 mOsm and 450 mOsm, more preferably between 230 and 330 mOsm. Ocular formulations containing combinations of norketotifen and cyclosporine are now presented and contain norketotifen in concentrations preferably between 0.01 percent and 0.50 percent (as base), more preferably between 0.01 percent and 0.1 percent in combinations with cyclosporine in concentrations preferably between 0.01 percent and 0.1 percent, more preferably approximately 0.05 percent (as base).

Accordingly, in certain embodiments, ocular formulations comprising therapeutically effective amounts of norketotifen for treating dry eye disorder in mammals are provided, as are methods of treating dry eye disorder by administering to mammals in need thereof with therapeutically effective amounts of ocular formulations comprising norketotifen.

In certain embodiments, methods of reducing symptoms associated with dry eye are provided.

In certain embodiments, methods of decreasing contact lense intolerance are provided.

In certain embodiments, the ocular formulations also comprise a therapeutically effective amount of cyclosporine when combined with norketotifen.

DETAILED DESCRIPTION

The terms "disorder" and "disease" are used as synonyms herein.

The term "therapeutically effective (amount or dose)" refers to a dose that yields therapeutic benefit to patients, which in the present case refers to therapeutic benefit to patients suffering from xerophthalmic disorders. The actual amount of norketotifen yielding therapeutic benefit to a patient, suffering from xerophthalmia, varies with the length of time of the treatment, the administration form and the severity of the disease.

The term "norketotifen" as used herein, refers either to free base or a pharmaceutically acceptable salt form or solvate thereof. A preferred pharmaceutically acceptable salt of norketotifen is for example a hydrochloride, a hydrobromide, a hydrogen maleate, a hydrogen sulfate and a hydrogen fumarate. More preferred salts of norketotifen are the hydrochloride salts and the hydrogen fumarate salt. Most preferred is the hydrogen fumarate salt. The term "pharmaceutically acceptable salt" and the like refer to salts prepared from pharmaceutically acceptable acids, such as for example hydrochloric, hydrobromic, maleic, sulphuric and fumaric acids. They are generally safe for administering to humans according to established governmental standards, including those promulgated by the United States Food and Drug Administration. The term "solvate," as used herein, refers to a solid phase that contains solvent molecules in addition to norketotifen molecules in the crystal lattice. The terms "formulation(s)" and "composition(s)" are herein considered as being synonyms.

The term "norketotifen", as used herein, also refers to racemic norketotifen as well as the isomers thereof. The terms "isomer", "enantiomer" or "atropisomer" in this document refer to a single isomer, substantially free from the corresponding distomeric isomer and having an enantiomeric purity of ee (enantiomeric excess) of at least 90%. A more preferred enantiomeric purity is ee ≥95% and the most preferred enantiomeric purity is ee ≥98% (corresponding to a mixture of 99% of the eutomer and 1% of the distomer).

Most of the norketotifen formulations for ocular administration that are described herein can be readily processed by standard manufacturing processes, well known to those skilled in the art. The choice of an appropriate method for sterilization is within the scope of understanding of a person of ordinary skill in the art of manufacture of parenteral dosage forms. Thus, norketotifen compositions, which are stable to temperature, can be readily autoclaved post-processing of the formulation and filling into the final container.

Ophthalmic carriers are typically adapted for topical ophthalmic administration, and are for example water, mixtures of water and water-miscible solvents, such as C1- to C7-alkanols, vegetable oils or mineral oils comprising from 0.5 to 5 percent by weight ethyl oleate, hydroxyethylcellulose, carboxymethylcellulose, polyvinylpyrrolidone and other non-toxic water-soluble polymers for ophthalmic uses, such as, for example, cellulose derivatives, such as methylcellulose, alkali metal salts of carboxymethylcellulose, hydroxymethylcellulose, hydroxyethylcellulose, methylhydroxypropylcellulose and hydroxypropylcellulose, acrylates or methacrylates, such as salts of polyacrylic acid or ethyl acrylate, polyacrylamides, natural products, such as gelatin, alginates, pectins, tragacanth, karaya gum, xanthan gum, carrageenan, agar and acacia, starch derivatives, such as starch acetate and hydroxypropyl starch, and also other synthetic products, such as polyvinyl alcohol, polyvinyl pyrrolidone, polyvinyl methyl ether, polyethylene oxide, preferably cross-linked polyacrylic acid, such as neutral Carbopol, or mixtures of those polymers. Preferred carriers are water, cellulose derivatives, such as methylcellulose, salts of carboxymethylcellulose, hydroxymethylcellulose, hydroxyethylcellulose, methylhydroxypropylcellulose and hydroxypropylcellulose, neutral Carbopol, or mixtures thereof. A highly preferred carrier is water. The concentration of the carrier is, for example, from 1 to 100,000 times the concentration of the active ingredient.

Various diseases and circumstances may result in dry eyes and examples are keratoconjunctivitis sicca, age-related dry eye, contact lens intolerance, Stevens-Johnson syndrome, Sjögren's syndrome, ocular cicatrical pemphigoid, blepharitis, corneal injury, infection, Riley-Day syndrome, congenital alacrima, nutritional disorders or deficiencies (including vitamin A deficiency), autoimmune and other immunodeficient disorder, and side effects of medications. The methods disclosed herein are effective regardless of the etiology of the dry eyes being treated.

The embodiments disclosed herein include methods of increasing tear fluid and/or reducing xerophthalmia symptoms in patients in need thereof by the administration of formulations containing therapeutically effective amounts of norketotifen to said patients.

In accordance with certain embodiments, it is determined if a patient is suffering from a xerophthalmic (dry eye) disorder, and if said determination is positive, an ophthalmic composition comprising a therapeutically effective amount of norketotifen or a pharmaceutically acceptable salt of norketotifen is administered to that patient that is sufficient to achieve therapeutic effects of said compound in said subject. Said diagnosis of xerophthalmia can be performed by a qualified physician, using interviews, physical examination and/or application of a standardized test, such as for example Schirmer's test and fluorescein tests of tear break-up time. Reviews of the diagnosis of keratoconjunctivitis sicca can be found in The Merck Manual, 18th Edition, pp. 899-900 and in Wikipedia, September 2008 (http://en.wikipedia.org/wiki/Keratoconjunctivitis_sicca). Both documents are hereby incorporated in their entirety by reference. Methods for diagnosis of dry eyes can also be found in textbooks in opthalmology.

Formulations Containing Norketotifen

The terms "formulation" and "composition" in this document are considered synonyms and are used interchangeably.

The maximal solubility of norketotifen hydrogen fumarate in water has now been found to be 2.7 mg/ml and the corresponding figure was found to be 4.5 mg/ml when tested in saline. Thus, norketotifen is soluble in water up to and including the concentrations that are useful for ophthalmic indications. Ocular formulations of norketotifen have been described in U.S. Provisional Patent Applications No. 61/197,177, which is hereby incorporated in its entirety by reference. Ocular formulations of norketotifen to be used by individuals suffering from a dry eye syndrome may be hypotonic or isotonic. Thus, the acceptable osmolality may range from about 150 mOsm to about 350 mOsm. Tear osmolality in healthy individuals is usually around or slightly above 300 mOsm and is not significantly affected by age, as pointed out by Craig et al (1995), which publication is hereby incorporated in its entirety by reference.

Although norketotifen has ocular therapeutic activity after oral administration, it is a preferred method to administer a norketotifen formulation topically to the eye, for example as liquid drops, washes, gels, emulsions, sprays, ointments, or as a topical liposome formulations or by other means as described in the Provisional Patent Application No. 61/197,177. Norketotifen may also be administered to the eye via devices, such as for example pump-catheter systems, continuous ocular release devices or via contact lenses or minitablets or gel-forming minitablets. Preferred ocular formulations are solutions and emulsions.

Norketotifen can also be administered systemically to patients. Examples of systemic administration forms of norketotifen are liquids, emulsions or suspensions via nose drops, or nasal sprays. Suitable oral administration forms are for example regular tablets, capsules, syrups, as well as controlled-release formulations thereof. Suitable oral or nasal doses are from approximately 1 mg norketotifen to approximately 20 mg norketotifen as the free base or the equivalent amount of norketotifen in a salt form, such as for example a hydrogen fumarate salt. Norketotifen may also be injected intravenously or subcutaneously or intramuscularly or the drug can be administered via transdermal routes, using patches, creams and other transdermal formulations. Nose drops or nasal sprays will contain from 1.0 mg to 20 mg of norketotifen free base or the equivalent amount of norketotifen in a salt form, such as for example a hydrogen fumarate salt. Transdermal patches may deliver drugs continuously for up to 7 days using available technology, known to those skilled in the art (U.S. Pat. No. 7,270,830). The amount of norketotifen in a transdermal patch will depend on multiple factors, such as for example the delivery rates from the patch, the formulation of the active ingredient in the patch and the intended duration of the dermal delivery. Continuous transdermal delivery of norketotifen using transdermal patches for 24 to 96 hours is preferred and transdermal patches with an intended delivery time of up to 96 hours may contain 1 mg to 100 mg of norketotifen free base or the equivalent amount of norketotifen in a salt form, such as for example a hydrogen fumarate salt. Advantages of the transdermal patch delivery approach include application once every several days and avoidance of high peak plasma drug concentrations that may result in adverse events. The purpose of all systemic formulations is to achieve ocular concentrations of norketotifen that offer therapeutic effects to patients who are suffering from xerophthalmia. Upon systemic administration, the active compound will reach the ocular tissues after systemic absorption and distribution.

It has now been found that norketotifen surprisingly promotes tear flow, which is not believed to be a consequence of its antihistaminic activity since lacrimal epithelial histamine H-1 receptors have not been described and are not believed to exist. Furthermore, neither the antihistaminic nor the anti-inflammatory effects of olopatadine translated into increased tear flow, but olopatadine was actually reported to decrease tear flow (U.S. Pat. No. 7,247,623). The mechanism(s) for the surprising effects of norketotifen on tear flow are therefore not known.

As tear flow was significantly improved by administration of norketotifen, symptoms of dry eye disease will be ameliorated by the administration of norketotifen to patients suffering from xerophthalmia. It is an embodiment hereunder to obtain an amelioration of the symptoms of dry eye disorders by the administration of formulations containing therapeutically effective concentrations of norketotifen or combinations of norketotifen and cyclosporine.

It has now been found that after ocular applications, compositions of norketotifen offer therapeutic effects of long duration, making once to four times daily applications of the composition possible for the patient. Furthermore, it has now been found that stable compositions of norketotifen can be prepared in the preferred pH-range that does not cause irritation to the ocular tissues, said preferred pH range being from pH 4.6 to pH 6.0.

It is an objective of the embodiments disclosed herein to provide ocular compositions that deliver therapeutically effective concentrations of norketotifen to the ocular tissues and the lacrimal glands in therapeutic doses that allow administration once daily to four times daily, preferably one or two times daily and most preferred once daily administration. The new formulations that have been developed for norketotifen have therapeutic effects in patients in need thereof, while not causing ocular side effects, such a burning, redness or irritation, and while being stable upon storage.

The embodiments disclosed herein are useful for the treatment of subjects in need of medication for xerophthalmic disorders and for subjects suffering from ocular allergic disorders, such as for example allergic conjunctivitis.

The terms "patients" and "subjects" in this document refer to mammals, such as for example humans, dogs and cats. The term "therapeutically effective (dose)" refers to a dose that yields therapeutic benefit to patients, which in the present case refers to therapeutic benefit to patients suffering from xerophthalmia.

Using excipients that have now been found to be compatible with norketotifen, compositions such as topical ophthalmic solutions, topical ophthalmic gels, topical hydrophilic ophthalmic ointments, topical ophthalmic emulsions, topical ophthalmic liposome compositions were prepared and tested. A preferred norketotifen composition useful for patients suffering from xerophthalmia is as follows, where HF means Hydrogen Fumarate salt; EDTA is ethylenediaminetetraacetic acid (edetate); BAK is benzalkonium chloride. BAK may be replaced by HEX (polyhexamide hydrochloride) in the concentrations 0.001 to 0.1% (useful composition) or 0.01% to 0.02% (preferred composition):

| Norketotifen HF: | 0.0345% |
|---|---|
| EDTA: | 0.100% |
| Boric Acid: | 0.095% |
| BAK or HEX: | 0.010% |
| Sorbitol: | 4.6% |
| Water: | q.s. |
| pH: | 5.5 |

Most preferred is said composition without the preservative benzalkonium chloride.

Composition intended for sufferers of xerophthalmia may also contain, as an excipient, hyaluronic acid (MW 750,000 to 2,000,000 daltons) at concentrations from 0.01 percent to 5 percent, which is expected to further improve tear film break up time (Iester, 2000; Aragona, 2002). The term "tear film break up time" as used herein, refers to the time required for the ocular surface to lose cohesive surface wetting after each blink; dry areas will appear as the result of normal evaporation of tears in about 4 seconds and an urge to blink is triggered (Alcon, 2008). A preferred norketotifen composition useful for patients suffering from xerophthalmia and containing hyaluronic acid is as follows, where the preservative BAK (benzalkonium chloride) can be replaced with HEX (polyhexamide):

| Norketotifen HF: | 0.0345% |
|---|---|
| Hyaluronic Acid: | 0.400% |
| EDTA: | 0.100% |
| Boric Acid: | 0.095% |
| BAK or HEX: | 0.010% |
| Sorbitol: | 4.6% |
| Water: | q.s. |
| pH: | 5.5 |

Most preferred is said composition without the preservative benzalkonium chloride.

Combinations

Ophthalmic compositions of norketotifen may contain one or more additional, therapeutically active ingredients. In addition to norketotifen, such combination compositions may contain one or more anti-inflammatory drug, such as for example a steroid belonging to the class consisting of corticosteroids, such as for example rimexolone (Vexol®, Alcon), fluorometholone (generic), prednisolone acetate (generic), loteprednol etabonate (generic) and difluprednate (Durezol™, Sirion), or one or more NSAID, such as for example nepafenac (Nevanac™, Alcon), diclofenac (Voltaren™, Novartis), ketorolac (Acular™, Allergan), bromfenac (Xibrom™, Ista), ibuprofen (generic) and indomethacin (generic).

In addition to norketotifen, combination compositions may contain one or more immunosuppressants, such as for example cyclosporine (generic), tacrolimus (Protopic™, Fujisawa) or pimecrolimus (Elidel®, Novartis). Combinations of norketotifen and cyclosporine are preferred and the compounds norketotifen and cyclosporine can be combined in the same composition, as shown in Table 5, or can be administered separately, which will make it possible to administer individualized dosing to patients. Using a combination of norketotifen and the significantly more toxic compound cyclosporine will offer a cyclosporine-sparing effect to the patient and will open the possibility to obtain improved therapeutic activity without increasing the doses of cyclosporine.

In addition to norketotifen, such combination compositions may contain one or more compound with local anesthetic activity, such as for example lidocaine or bupivacaine.

All combination products using compositions described herein are included in the embodiments disclosed herein.

A preferred combination is a formulation that includes norketotifen and cyclosporine along with a pharmaceutically acceptable carrier. Compositions containing combinations of norketotifen and cyclosporine have now been prepared and tested (Example 6).

EXAMPLES

Example 1

Effects of Norketotifen and Ketotifen on Granulocyte Activation

Methods

In the present studies, effects on granulocyte activation were studied as inhibition of histamine release from human granulocytes (buffy coat) by norketotifen. The method is a modification of the method described by Nolte, H. et al., 1988. Granulocytes were obtained from human volunteers and mediator release was induced by incubation (20 min/37° C.) with the calcium ionophore A23187 (5 µM) in the presence or absence of a test article. Histamine was selected as an indicator for mediator release because of the ease with which histamine can be analyzed, using commercially available kits. The test articles were evaluated, in duplicate, at five concentrations and IC50-values were calculated.

Results

Norketotifen (IC50=9.2 µM) was approximately 10 times more active than ketotifen (IC50=91 µM) in inhibiting A23187-mediated granulocyte activation.

TABLE 1

Inhibition of histamine release.

| Test Article | Inhibition of mediator release IC50 (µM) |
| --- | --- |
| RS-ketotifen | 91 |
| RS-norketotifen | 9.2 |

Conclusions

The calcium ionophore A23187 was used to increase intracellular calcium concentration of the granulocytes. Those skilled in the art of pharmacology realize that the presently used A23187-method mimics in vivo granulocyte activation, initiated by IgE- and cAMP-induced increase in the intracellular calcium concentration, which in turn triggers a release of inflammatory mediators (such as histamine) from intracellular granulae, which is a process that is usually referred to as granulocyte "activation." The concentrations of norketotifen and ketotifen used here had to be relatively high, since the validated method for in vitro granulocyte activation uses high concentrations, temperature and exposure time for the calcium ionophore.

Norketotifen was significantly more potent than ketotifen as an inhibitor of activation of human granulocytes. It is not known if mast cell inhibition per se is related to the effects of norketotifen on dry eyes. Olopatadine is an inhibitor of the release histamine from mast cells (Patanol®, Alcon; Packet Insert, 2007) and is a known mast cell stabilizer (Rosenwasser et al., 2005) that reduces tear flow (U.S. Pat. No. 7,247,623).

Example 2

Antihistaminic Activity In Vivo

Methods

Male rats (150-200 g) were starved overnight and twelve hours after dorsal depilation, the animals were orally pretreated with the test compound(s). Four dorsal test areas were marked with permanent ink, carefully avoiding the area closest to the spine. Exactly 60 min after the dosing of the test compound, two intradermal injections of histamine (50 microliter; 1.0 mg/ml of histamine di-HCl) were performed, one on each side on the back of the animal. Two intradermal injections of the vehicle for the histamine solution were also performed. Evans blue dye (20 mg/kg) was injected iv 1 minute prior to the intra-dermal injections of histamine and the histamine vehicle. Twenty minutes were allowed for the wheal response to fully develop, whereupon the animals were euthanized and the dorsal skin containing the intradermal wheals were deflected. The blue spotted areas were measured in square millimeters and the duplicate vehicle wheal responses were averaged. In vehicle-treated animals, the wheal area, on average, was increased by histamine by 98 mm$^2$. The inhibition was calculated in percent difference from this baseline value.

Results

TABLE 2

Antihistaminic activity in vivo after oral dosing of test compounds

| Test compound Dose (mg/kg) | Histamine (mm$^2$) | Saline (mm$^2$) | Histamine effect (mm$^2$) | Inhibition (%) |
| --- | --- | --- | --- | --- |
| Vehicle* | 122 ± 9 | 24 ± 2 | 98 | — |
| Vehicle** | 107 ± 4 | 25 ± 1 | 82 | — |
| Ketotifen; 1 | 68 ± 6 | 21 ± 2 | 47 | 43 |
| Ketotifen; 10 | 24 ± 2 | 22 ± 3 | 2 | 97 |
| Norketotifen; 1 | 114 ± 8 | 22 ± 1 | 92 | 6 |
| Norketotifen; 10 | 39 ± 2 | 22 ± 1 | 17 | 83 |
| Norketotifen; 50 | 10 ± 1 | 12 ± 1 | 0 | 100 |
| DPH***; 10 | | | | 31 |

*Vehicle for norketotifen.
**Vehicle for ketotifen.
***Diphenhydramine; previous experiment Conclusions The dose/response curves were not parallel. At IC$_{75}$, ketotifen was approximately twice as potent as norketotifen as an antihistamine. It is not known if the therapeutic effects of norketotifen in xerophthalmia are related to the antihistaminic effects of the compound. Thus, steroids and the immuno-suppressant cyclosporine have therapeutic effects in patients suffering from dry eye disease, but neither have antihistaminic activity. It is also concluded that norketotifen was well absorbed in rats after oral administration.

Example 3

Antimuscarinic (M-1) Activity

Methods

Experiments were carried out on membranes from SF9 cells that had been infected with baculovirus to express the human recombinant muscarinic M-1 receptors. After incubation with the test article and a radioligand and after washing, bound radioactivity was determined with a liquid scintillation counter, using a commercial scintillation cocktail. The specific binding was defined as the difference between total binding and nonspecific binding in the presence of excess of unlabelled ligand. IC$_{50}$ values (concentrations required for 50 percent inhibition of specific binding) were determined by non-linear regression analysis of the competition curves.

Results

TABLE 3

Antimuscarinic activity in vitro on human M-1 receptors.

|  | IC50 (nM) |
|---|---|
| KETOTIFEN | 305 |
| NORKETOTIFEN | 1,440 |
| DESLORATADINE (Clarinex ®) | 62 |

Conclusions

Norketotifen has some antimuscarinic activity, although significantly less than ketotifen. The known and potent antimuscarinic activity of desloratadine was confirmed, thereby validating the test methodology. In a study that was similar to the current Example, Wolff et al found that IC50 for the antimuscarinic activity was 217 nM, 1742 nM and 65 nM, respectively for ketotifen, olopatadine and desloratadine (Wolff et al. 2007).

Example 4

Effects of Norketotifen on Tear Flow

Methods

Inbred mice (N=8/group) were administered a solution of norketotifen HF (Bridge Pharma Inc, Sarasota, Fla.), ketotifen HF or vehicle (saline) into the right eye. The concentration of norketotifen HF and ketotifen HF in the test solution was 0.07%, corresponding to 0.05% of the free base. All instillations were performed twice daily and consisted of 0.05 mL. A total of five instillations were administered. Tear measurements were performed 45 minutes after the first drug instillation on Day 3, by carefully placing the bent end of a Zone-Quick phenol red impregnated cotton thread (FCI Ophthalmics, Pembrooke, Mass.) at the intercanthus of the eye and holding it in place for 30 seconds. After removal, the length of the red area of the thread was measured in millimeters. During tear measurements, all animals were lightly anesthetized with isoflurane in order to reduce movement and stress. Ketotifen was tested in an additional group of eight mice in parallel to norketotifen; the ketotifen concentration was the same as the concentration of norketotifen.

Results

Forty-five minutes after the 5th treatment, the modified Schirmer's test demonstrated statistically significant effects of norketotifen (P<0.05) but not of ketotifen (P>0.05).

TABLE 4

Effects on tear flow in rodents.

| | N | Conc. (%) | Mean ± SEM (mm) | p |
|---|---|---|---|---|
| VEHICLE | 8 | — | 3.88 ± 0.125 | — |
| KETOTIFEN HF | 8 | 0.07 | 4.25 ± 0.250 | 0.20 |
| NORKETOTIFEN HF | 8 | 0.07 | 4.62 ± 0.263 | 0.02 |

Conclusions

Repeated treatment with norketotifen caused an increase in tear flow (Schirmer scores) with statistical significance after five treatments. This is a surprising effect, particularly since healthy animals were used in this study.

Example 5

Ocular Topical Formulations Containing Norketotifen

The compatibility of numerous excipients with norketotifen has been studied. Ocular compositions that are topically administrable may be for example, solutions, hydrophilic or hydrophobic ointments, emulsions, or liposome compositions. Topically administrable solutions may be preferred. Compositions according to Table 4 are examples of useful norketotifen solution compositions for ocular instillation to patients suffering from dry eye syndrome. Thus norketotifen HF will be in a concentration range from 0.01% to 0.50%, preferably 0.01 to 0.10% and most preferred 0.034% to 0.035%. Sodium edetate in a concentration from, 4% to 0.05%, preferably from 2% to 0.05%, and most preferred 0.1% can be used as a stabilizer and chelating agent. Boric acid/borate can be used as a buffer and a preservative in concentrations of 4% to 0.01%, preferably 1% to 0.05% and most preferred 0.095%. If a preservative excipient is needed, for example a stabilized oxychloro complex or benzalkonium chloride (BAK) or polyhexamide hydrochloride (HEX) may be used. A useful concentration of a stabilized oxychloro complex is from 0.01% to 0.003%. A useful concentration of BAK is from 0.05% to 0.001%, preferably 0.02% to 0.005% and most preferred 0.01%. A useful concentration of polyhexamide (polyhexa-methylene biguanide; HEX) is from 0.001% to 0.1%, preferably 0.01% to 0.02%. It will, however, be advantageous if a composition without any preservative can be used (Noeker et al., 2006; which publication is hereby incorporated in its entirety by reference). An example of a suitable tonicity and viscosity modifier is sorbitol that may be useful in concentrations of 10% to 1%, preferably 5% to 2% and most preferred at 4.6%. The acidity of the formulation can be adjusted with any pharmaceutically acceptable acid or base and the pH of composition should be between pH 4.0 and pH 7.0, preferably between pH 4.6 and pH 6.0 and most preferred approximately pH 5.5 and as mentioned above, boric acid/borate may be used as a buffering system. The osmolality of the composition should preferably be between 230 and 330 mOsm. The free base of norketotifen may be used, but a salt form is preferred, most preferred is the hydrogen fumarate salt (HF) of norketotifen.

TABLE 5

Examples of topical ocular formulations of norketotifen for dry eye syndrome. Composition concentrations are expressed as % w/w. Osmolality is expressed as mOsm/kg. Preservatives are preferably avoided. Norketotifen hydrogen fumarate 0.0345% corresponds to 0.025% of norketotifen free base. BAK may be replaced by HEX (polyhexamide hydrochloride) in the concentrations 0.001 to 0.1% (useful composition) or 0.01% to 0.02% (preferred composition or 0% (most preferred composition)

| | Useful Comp. | Preferred Comp. | Most Preferred Comp. |
|---|---|---|---|
| Norketotifen HF | 0.01 to 0.5% | 0.01 to 0.1% | 0.0345% |
| Sodium edetate | 0.05 to 4% | 0.5 to 2 | 0.1% |
| Boric acid | 0.01 to 4% | 0.05 to 1% | 0.095% |
| BAK | 0.001 to 0.05% | 0.005 to 0.05% | 0.00% |
| Sorbitol | 1 to 10% | 2 to 5% | 4.6% |
| Water | q.s. | q.s. | q.s. |
| pH | 4.6-6.0 | 4.6-6.0 | 5.5 |
| Osmolality | 230-330 | 230-330 | 230-330 |

Comp. = Composition.
HF = Hydrogen Fumarate salt.
BAK = Benzalkonium chloride

Example 6

Ocular Combination Formulations Containing Norketotifen

The compatibility of norketotifen with numerous APIs (active pharmaceutical ingredients) and excipients has been studied.

A norketotifen formulation, suitable for use by patients suffering from dry eye syndrome, may contain hyaluronic acid (MW 750,000 to 2,000,000 daltons) that will further improve tear break-up time. A useful hyaluronic acid or an acetylated hyaluronic acid (MW 10,000 to 1,000,000; preferably about 100,000 and preferably with an acetyl group substitution number between 3.0 and 3.5. The concentration of hyaluronic acid in the ophthalmic composition is from 0.01% to 10% (w/w). A norketotifen formulation may also contain a corticosteroid, such as for example loteprednol etabonate, 0.2% (Alrex®, Bausch and Lomb) or loteprednol etabonate, 0.5% (Lotemax®, Bausch and Lomb).

An ophthalmic formulation, suitable for use by patients suffering from dry eye syndrome may contain norketotifen in combination with an immuno-suppressant drug, such as for example cyclosporine. Sufficient concentrations of norketotifen in said combination formulation to achieve therapeutic effect against xerophthalmia are from approximately 0.005% to approximately 0.05% (as base). Sufficient concentrations of cyclosporine in said combination formulation to achieve therapeutic effect against xerophthalmia are from approximately 0.01% to approximately 0.1% (as base). Various concentrations of norketotifen and cyclosporine may be used in combination formulations since the severity of the xerophthalmic disease may differ between patients and over the time course of the disease for individual patients. Thus, a patient with acute and severe xerophthalmia may be started with a composition containing one or both of the active ingredients—norketotifen and cyclosporine—in high concentrations and later be switched to a composition that contains lower concentrations of one or both of the active therapeutic ingredients. Since cyclosporine is not water-soluble, various emulsion formulations containing both cyclosporine and norketotifen have now been prepared and tested.

TABLE 6

Examples of compositions containing norketotifen and cyclosporine

|  | Batch 81114-1 | Batch 81117-1 | Batch 81117-2 |
|---|---|---|---|
| NORK hydrogen fumarate | 0.0208%[1] | 0.0208%[1] | 0.0208%[1] |
| Cyclosporine | 0.05% | 0.05% | 0.05% |
| Glycerin | 1.75 | 1.75 | 1.75 |
| Sodium citrate | 0.30 | 0.30 | 0.30 |
| 1.0 N HCl | q.s.[2] to pH 5.0-6.0 | q.s.[2] to pH 5.0-6.0 | q.s.[2] to pH 5.0-6.0 |
| Castor oil | 5.00 | 5.00 | 5.00 |
| Polysorbate 80 | 4.00 | 4.00 | 4.00 |
| Benazalkonium chloride | — | 0.010 | — |
| Methylparaben | — | — | 0.017 |
| Propylparaben | — | — | 0.017 |
| Water | q.s.[2] | q.s.[2] | q.s.[2] |

[1]Equivalent to 0.015% of free base;
[2]quantum sufficit

The formulations were prepared by adding cyclosporine to castor oil plus polysorbate 80 and mixing until the drug substance was dissolved. In a separate container, glycerin, water, and sodium citrate were combined. NORK was added to the aqueous solution and mixed until dissolved. The pH of the aqueous solution was then adjusted with HCl to pre-determined acidity, which could be between pH 4.0 and pH 7.0, usually was between pH 5.0 and pH 6.0 and preferably was about pH 5.5. The aqueous solution was added to the castor oil solution and mixed vigorously to form a coarse emulsion. Next, the coarse emulsion was sonicated with a ¼" ultrasonic probe (Sonics Inc. Vibra Cell) for 5 minutes. In compositions where a preservative was used, it was added to the emulsion and mixed until homogenous. Tests demonstrated that the resulting emulsion droplets were less than 1.0 micron.

Equivalents

When used as therapy for dry eye syndrome, norketotifen can also be administered orally or nasally, using doses of norketotifen HF that correspond to 1.0 mg to 20 mg norketotifen base, in formulations as described in the Provisional Patent Application 61/197,177, which is hereby incorporated in its entirety by reference.

Given the fact that norketotifen and the isomers thereof have been found to have beneficial effects in xerophthalmia, it can be anticipated that other drugs with similar pharmacological profiles may also have similar effects for the treatment of Xerophthalmia. Thus, for example fexofenadine, epinastine, azelastine, olopatadine, ketotifen and cetirizine and the possible isomers thereof, used per se in appropriate formulations or in combinations with corticosteroids, immunosuppressants or drugs with similar pharmacological effects, may be anticipated to have therapeutic effects in patients suffering from various forms of xerophthalmia.

What is claimed is:

1. A method for treating xerophthalmia in a subject by increasing tear production. comprising topically administering to an eye of said subject in need thereof an ophthalmic formulation comprising a therapeutically effective amount of norketotifen or a pharmaceutically acceptable salt of said compound, wherein the norketotifen or pharmaceutically acceptable salt thereof increases tear production in the subject.

2. The method of claim 1, wherein said pharmaceutically acceptable salt is the hydrogen fumarate or hydrochloride salt of norketotifen.

3. The method of claim 1, wherein said treatment of xerophthalmia further comprises an improvement in a symptom associated with xerophthalmia selected from the group consisting of ocular dryness, ocular burning, sandy-gritty eye irritation, ocular foreign-body sensation and photophobia.

4. The method of claim 3, wherein said administration results in an improvement of xerophthalmia based on Schirmer scores.

5. The method of claim 1, wherein said subject is a human.

6. The method of claim 1, wherein said topical administration is to the mucosal surfaces of the eye and the conjunctival membranes of the eye.

7. The method of claim 1, wherein said therapeutically effective amount is 0.01 percent to 0.5 percent (w/v) of norketotifen.

8. The method of claim 1, wherein the tonicity of said formulation is between 150 mOsm and 450 mOsm.

9. The method of claim 1, wherein the acidity of said formulation is between pH 4.0 and pH 7.

10. A method for treating xerophthalmia in a subject by increasing tear production, comprising determining whether said subject suffers from a xerophthalmic disorder, and if said determination is positive, topically administering to an eye of said subject in need thereof an ophthalmic formulation comprising a therapeutically effective amount of norketotifen or a pharmaceutically acceptable salt of said compound, wherein the norketotifen or pharmaceutically acceptable salt thereof increases tear production in the subject.

11. A method for increasing tear flow in a subject, comprising topically administering to an eye of said subject in need thereof a formulation comprising a therapeutically effective amount of norketotifen or a pharmaceutically acceptable salt of said compound, wherein the norketotifen or pharmaceutically acceptable salt thereof increases tear production in the subject.

12. A method for treating xerophthalmia in a subject by increasing tear production, comprising topically administering to an eye of said subject in need thereof an ophthalmic formulation comprising a therapeutically effective amount of norketotifen or a pharmaceutically acceptable salt of said compound as the sole therapeutically active agent against xerophthalmia, wherein the norketotifen or pharmaceutically acceptable salt increases tear production in the subject.

13. The method of claim 12, wherein said pharmaceutically acceptable salt is the hydrogen fumarate salt of norketotifen.

14. The method of claim 12, wherein said treatment of xerophthalmia further comprises an improvement in a symptom associated with xerophthalmia selected from the group consisting of ocular dryness, ocular burning, sandy-gritty eye irritation, ocular foreign-body sensation and photophobia.

15. The method of claim 12, wherein said administration results in an improvement of xerophthalmia based on Schirmer scores.

16. The method of claim 12, wherein said subject is a human.

17. The method of claim 12, wherein said subject is a dog or cat.

18. The method of claim 1, wherein said subject is a dog or cat.

* * * * *